United States Patent [19]
Kilis et al.

[11] Patent Number: 5,622,164
[45] Date of Patent: Apr. 22, 1997

[54] AIR FLOW RECORDER, GENERATOR AND ANALYSIS SYSTEM FOR INHALATION DEVICE TESTING AND MODELING

[75] Inventors: David Kilis, St. Paul; Harold E. Stone, White Bear Lake, both of Minn.

[73] Assignee: Minnesota Mining and Manufacturing Company, St. Paul, Minn.

[21] Appl. No.: 197,365

[22] Filed: Feb. 16, 1994

Related U.S. Application Data

[63] Continuation of Ser. No. 883,182, May 15, 1992, abandoned.

[51] Int. Cl.⁶ .......................... G09B 23/28; A61M 15/00; A62B 7/00; A62B 9/00
[52] U.S. Cl. .............................. 128/200.24; 128/202.13; 434/262
[58] Field of Search .................... 128/200.23, 200.24, 128/204.18, 204.21, 204.23, 719, 716, 725, 630, 202.13; 434/262

[56] References Cited

U.S. PATENT DOCUMENTS

| | | | |
|---|---|---|---|
| 3,896,792 | 7/1975 | Vail et al. | 128/719 |
| 4,036,221 | 7/1977 | Hillsman et al. | 128/204.23 |
| 4,345,612 | 8/1982 | Koni et al. | 128/204.21 |

(List continued on next page.)

FOREIGN PATENT DOCUMENTS

| | | | |
|---|---|---|---|
| 1235041 | 4/1988 | Canada. | |
| 2024477 | 8/1991 | Canada. | |
| 2403616 | 8/1974 | Germany | 128/204.18 |
| 2131774 | 5/1990 | Japan. | |
| 462366 | 6/1990 | Sweden. | |
| 1243727 | 7/1986 | U.S.S.R. | 128/200.24 |
| 2113101 | 11/1985 | United Kingdom. | |

OTHER PUBLICATIONS

"Apparatus for the Control of Breathing Patterns During Aerosol Inhalation", by Phipps et al. Journal of Aerosol Medicine, vol. 5, No. 3, 1992 pp. 155–170.

Myojo, T., "Breathing Pattern Simulation Using Slit/Cam Valve", pp. 240–244, American Industrial Hygiene Assoc. J. (1989), 50(5).

Davis, J.N., "Interrelationships of the Volume and Time Components of Individual Breaths in Resting Man", pp. 481–498, J. Physiology, vol. 245, No. 2 (1975).

Kondo, T., et al., "A Computerized Standard Flow–Generator for Spirometer Calibration", pp. 409–416, J. Exp. Clin. Med (Japan), vol. 14, Nos. 5–6 (1989).

(List continued on next page.)

*Primary Examiner*—Kimberly L. Asher
*Attorney, Agent, or Firm*—Gary L. Griswold; Walter N. Kirn; Jeffrey J. Hohenshell

[57] ABSTRACT

An air flow device for use in recording, analyzing, replicating, and generating breathing patterns. A piping structure provides receipt and transfer of pressurized gas through the device. The piping structure has a source connection for receiving a single constant source of pressurized gas. Aspirators are connected to the piping structure for receiving pressurized gas from the source connection and for selectively creating an output pressurization comprising a positive pressure gas flow and a negative pressure gas flow at a proportional solenoid valve. A balancing valve is connected to the piping structure for controlling and calibrating the output pressurization of the aspirators. A control system provides control of the aspirators, the balancing valve, and a solenoid valve. A solenoid valve is mechanically connected to the piping structure with pneumatic input and output connections and electronically connected to the control system with data input and output connections. The solenoid valve provides patterned pneumatic flow between the aspirators and a system model according to air flow commands received by the solenoid from the control system. The system model, in one embodiment, is a breath actuated inhaler device.

13 Claims, 7 Drawing Sheets

U.S. PATENT DOCUMENTS

| | | | |
|---|---|---|---|
| 4,444,201 | 4/1984 | Itoh | 128/716 |
| 4,513,295 | 4/1985 | Jones et al. | 128/630 |
| 4,635,631 | 1/1987 | Isumi | 128/204.23 |
| 4,648,395 | 3/1987 | Sato et al. | 128/204.23 |
| 4,681,100 | 7/1987 | Brychta et al. | 128/204.25 |
| 4,726,366 | 2/1988 | Apple et al. | 128/204.21 |
| 4,768,506 | 9/1988 | Parker et al. | 128/303 R |
| 4,796,467 | 1/1989 | Burt et al. | 128/200.24 |
| 4,838,257 | 6/1989 | Hatch | 128/204.18 |
| 4,846,166 | 7/1989 | Willeke | 128/200.24 |
| 4,848,332 | 7/1989 | Champain | 128/204.21 |
| 4,878,388 | 11/1989 | Loughlin et al. | 434/262 |
| 4,972,842 | 11/1990 | Korten et al. | 128/200.24 |
| 4,984,158 | 1/1991 | Hillsman | 128/725 |
| 4,996,980 | 3/1991 | Frankenberger et al. | 128/200.24 |
| 5,000,173 | 3/1991 | Zalkin et al. | 128/204.21 |
| 5,111,809 | 5/1992 | Gamble et al. | 128/204.18 |
| 5,167,506 | 12/1992 | Kilis et al. | 434/262 |

OTHER PUBLICATIONS

Proceedings of the 18th DOE Nuclear Airborne Waste Management and Air Cleaning Conference, "Evaluation of Methods, Instrumentation and Materials Pertinent to Quality Assurance Filter Penetration Testing", pp. 1131–1143, vol. 2 (1985), Scripsick et al, Los Alamos Nat'l Lab.

Horri, Y. et al., "Analysis of Airflow and Air Volume During Continuous Speech", p. 477, Behavior Research Methods and Instrumentation, vol. 7, No. 5 (1975).

Appel, E., "A Device for Measurement of Human Pulmonary Ventilation with Low Flow Resistance", International Conference on Biomedical Transducers, Pt. I, pp. 389–394, (1975), Inspec.

Bonnet, P., et al., "A Programmed Feedback Control of Solvent Vapour Concentrations in Experimental Inhalation Chambers", pp. 297–302, J. Appl. Toxicology, vol. 7, No. 5, (1987).

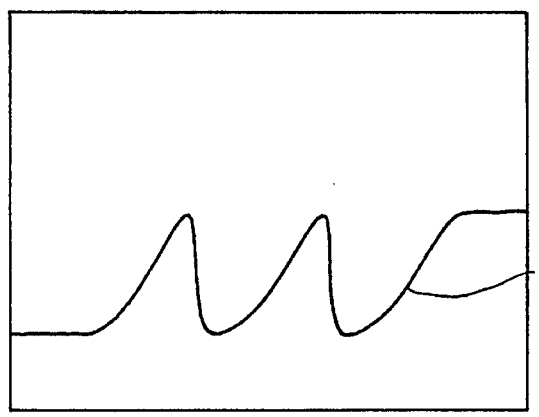
*Fig. 8a*
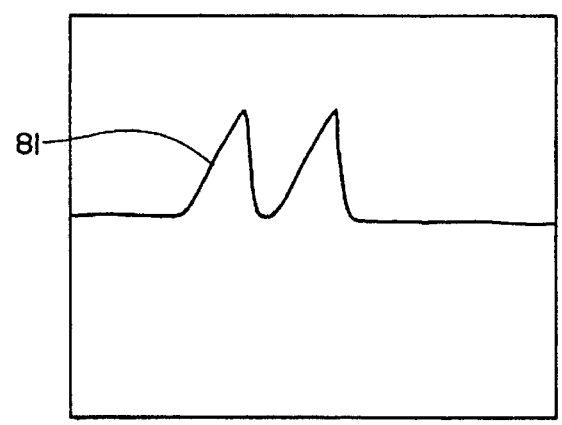
*Fig. 8b*
*Fig. 9a*
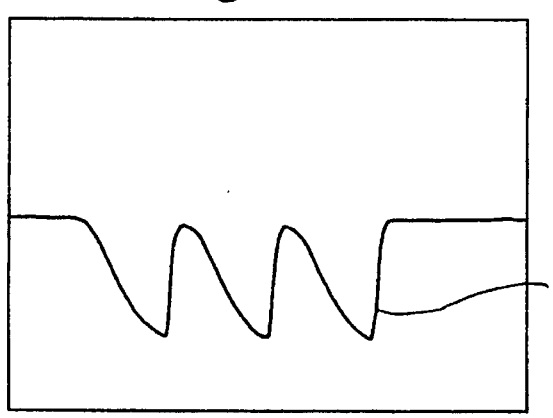
*Fig. 9b*
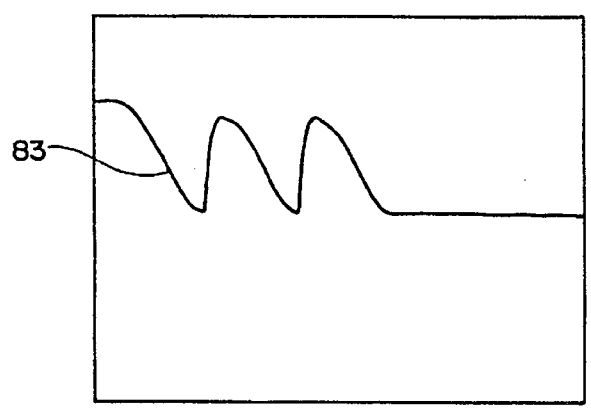

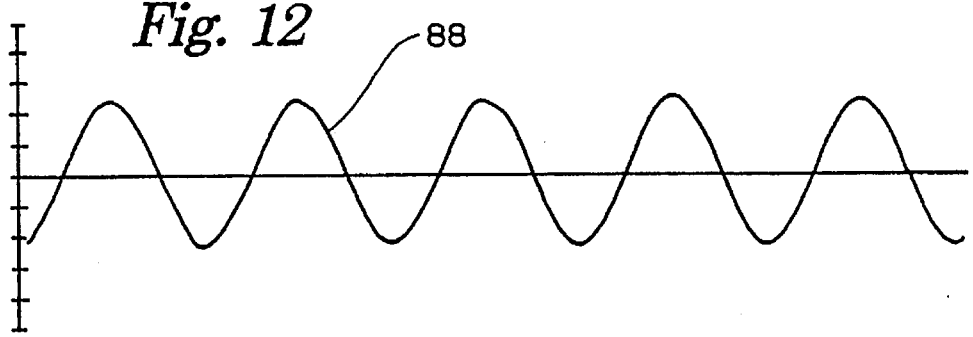
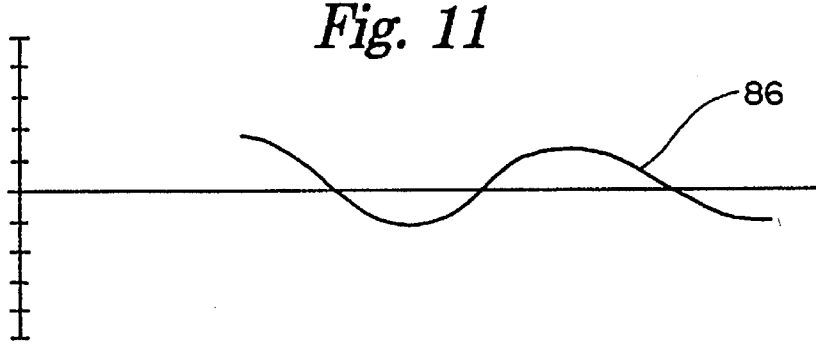
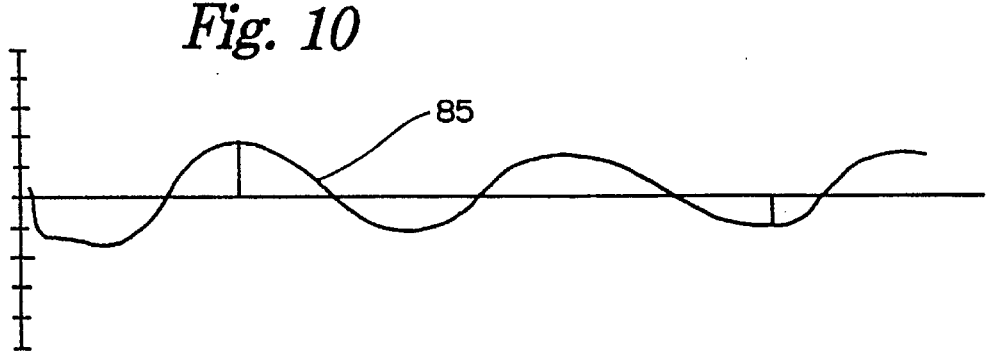

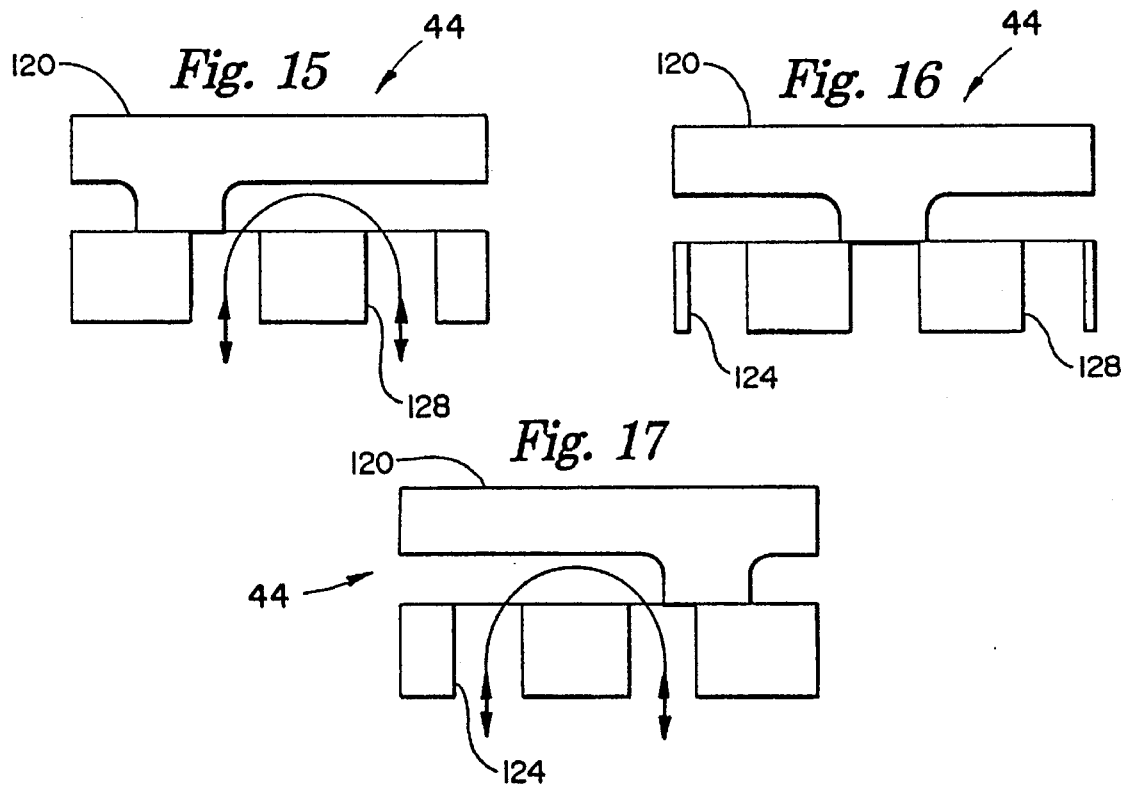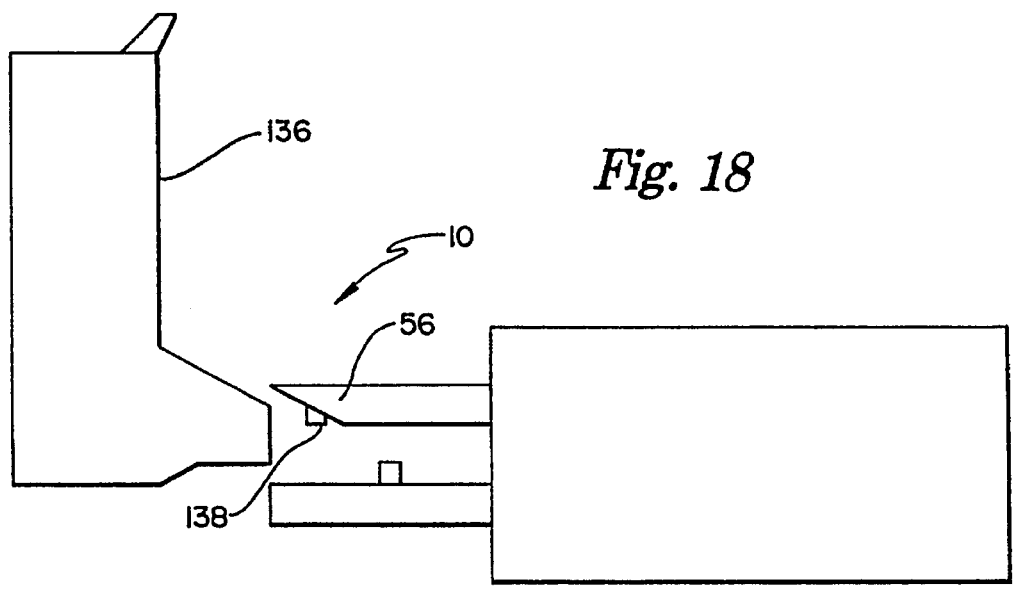

AIR FLOW RECORDER, GENERATOR AND ANALYSIS SYSTEM FOR INHALATION DEVICE TESTING AND MODELING

This is a continuation of application Ser. No. 07/883,182 filed May 15, 1992, now abandoned.

FIELD OF THE INVENTION

An air flow system which utilizes a single constant pressure source and regulates pressure and vacuum utilizing aspirators, a balancing valve, and a solenoid valve to record, store, replicate, and generate recorded air flow patterns.

BACKGROUND OF THE INVENTION

Various systems exist for breathing pattern simulation. These systems comprise either a pistoncylinder type device, a bellows type device, or a cam component. The piston-cylinder and bellows type systems are limited to symmetrical inspiration and expiration, as well as being limited to fixed volume uses. The cam operated systems require changing cams in order to change the magnitude of the breathing pattern generated.

SUMMARY OF THE INVENTION

This invention is an air flow device for use in recording, analyzing, replicating, and generating breathing patterns. A piping structure is provided for receipt and transfer of pressurized gas through the device. The piping structure has a source connection for receiving a single constant pressure source of pressurized gas. Aspiration means is connected to the piping structure for receiving pressurized gas from the source connection and for selectively creating an output pressurization comprising a positive pressure gas flow and a negative pressure gas flow at a proportional solenoid valve. A balancing valve is connected to the piping structure for controlling and calibrating the output pressurization of the aspiration means. Control means is also provided for controlling the aspiration means, the balancing valve, and a solenoid valve. A solenoid valve is mechanically connected to the piping structure with pneumatic input and output connections and electronically connected to the control means with data input and output connections. The solenoid valve provides patterned pneumatic flow between the aspiration means and a system model according to air flow commands received by the solenoid from the control means. The system model, in one embodiment, is a breath actuated inhaler device.

BRIEF DESCRIPTION OF THE DRAWINGS

FIG. 8a is a plot of an increasing ramp vacuum pattern.

FIG. 8b is a plot of an increasing ramp pressure pattern.

FIG. 9a is a plot of a decreasing ramp vacuum pattern.

FIG. 9b is a plot of a decreasing ramp pressure pattern.

FIG. 10 is a single frame plot of a recorded flow breathing pattern captured one frame at a time.

FIG. 11 is a single frame plot of a recorded flow breathing pattern permitting selective reconstruction of patterns.

FIG. 12 is a plot of a breathing pattern generated in the record mode of the air flow system operation.

FIG. 15 is a schematic view of a solenoid valve in the air flow system in a first position.

FIG. 16 is a schematic illustration of the solenoid valve of the air flow system shown in a neutral position.

FIG. 17 is a schematic illustration of the solenoid valve of the air flow system shown in a second pressurized position.

FIG. 18 is a schematic side elevation view of the air flow system using an inhaler device as the system model component.

DETAILED DESCRIPTION OF THE INVENTION

Figure 1:
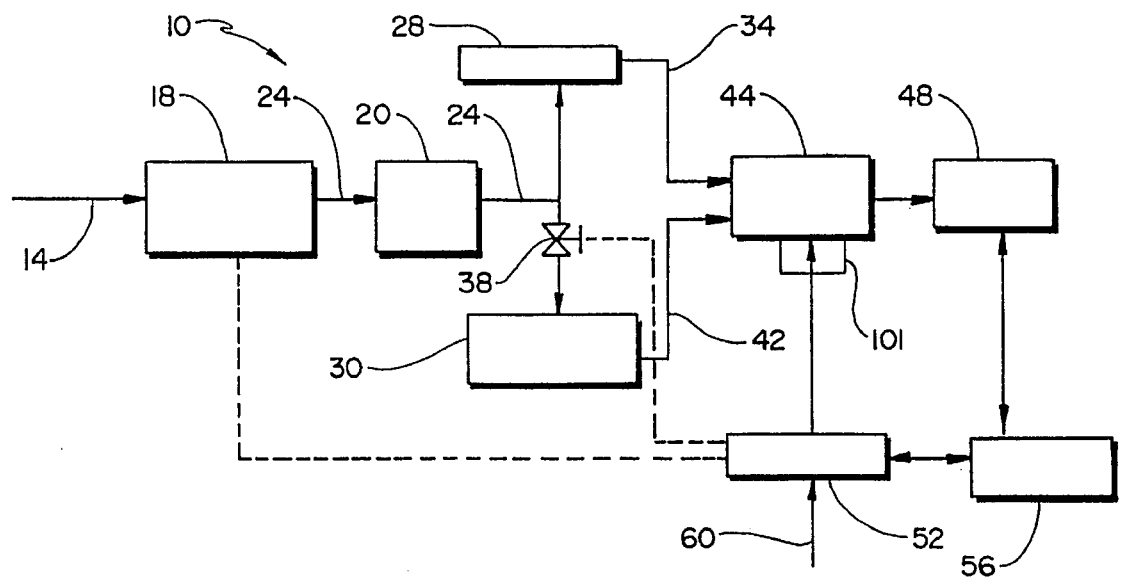
FIG. 1 is a schematic illustration of the air flow system of this invention.

FIG. 1 illustrates air flow system 10 designed for recording, storing, generating, and/or analyzing air flow patterns relating to breathing functions. Air flow system 10 uses and displays inspiratory and expiratory flows, normal and impaired breathing patterns, electronically altered air flow patterns, and air flow patterns having a wide variety of frequency and amplitude irregularities. Air flow patterns are also varied by environmental conditions, such as heat, humidity, particulates, and other factors which may be simulated by air flow system 10.

The solid lines in FIG. 1 represent gas flow or signal flow between the different components of air flow system 10, and the dashed lines represent signals and controls which may be automated. Air flow system 10 is designed for simple, portable, and inexpensive operation.

Pressure source 14 provides a pneumatic supply or air source for operation of air flow system 10 and is preferably a constant pressure source common to laboratory and medical provider environments. A variable pressure source may be utilized, but is not preferred. Pressure source 14 preferably comprises an air pressure source, although other gases may be substituted within the scope of this invention. Pressure regulator 18 regulates the pressure of the output gas of pressure source 14, and in doing so determines a maximum pressure to be utilized by other components of air flow system 10. Filter 20 filters the gas received from pressure source 14 and regulator 18.

Gas flow within piping structure 24 exits filter 20 and is routed to aspirator 28 and reverse aspirator 30. Aspirator 28 and reverse aspirator 30 represent gas actuated pressure devices which are configured for a pressurized gas output according to various specifications of a system. These devices in air flow system 10 are preferably operated using the venturi principle or other simple means for generating positive or negative pressure outputs. In air flow system 10, aspirator 28 receives a positive pressure gas source and outputs a negative pressure gas, as represented by vacuum line 34. Reverse aspirator 30 receives a positive pressure gas input via balancing valve 38 and outputs a positive pressure gas represented by pressure line 42. Piping structure 24 provides means for routing pressurized gas through air flow system 10.

Air flow system 10 may comprise only a single aspirator 28 and still be functional. However, use of reverse aspirator 30 is helpful to create symmetrical rates of change in flow rate outputs from solenoid valve 44 between positive and negative pressure signals. Without reverse aspirator 30, the volume (capacitance) or pressure loss (resistance) of aspirator 28 creates an asymmetrical rate of change in the flow rate output from solenoid valve 44, notwithstanding a constant rate of change of a piston position or movement within the solenoid valve. Although mathematical means may be used to eliminate this asymmetry, many solutions are required to predict and achieve symmetry due to the numerous possible piston positions and signals. Therefore, it is discovered that use of a reverse aspirator 30 to create volumes and time responses matched to aspirator 28 obviates the burdensome mathematical and related processing components otherwise needed to predict and achieve symmetry. Indeed, a single device, such as a capacitance adjusting shunt, could also be used to achieve this novel function.

Balancing valve 38 provides air flow system 10 with a capability of mechanically adjusting for any asymmetry between positive and negative pressure gases and signals. As shown in FIG. 1, this adjustment may be performed locally at the balancing valve or remotely via control means 52. Adjustments for asymmetry using balancing valve 38 may be complimented by symmetry-related adjustments using the electronics of control means 52, or vice versa.

A user of air flow system 10 may not know the values of asymmetry for the model or application being applied. However, if these values are known prior to operation of the system, then it is convenient and advantageous to pre-set offset values for the asymmetric flow into balancing valve 38 to achieve system symmetry. This feature enhances ease of operation, while encouraging very precise analysis. Balancing valve 38 is also used for adjusting peak flow rate of the pressurized gas flow. This feature is a substantial improvement in this technology field, particularly when used in combination with the other simulation and replication capabilities of air flow system 10.

Solenoid valve 44 is preferably configured as an efficient single piston proportional solenoid valve, although other valve configurations may be functional within the scope of this invention. Solenoid valve 44 is designed to selectively provide both positive and negative pressure gases to a system model 48. Solenoid valve 44 interacts with control means 52, which preferably comprises computational/analytic equipment and related display(s). System model 48 may be any one of various components, subsystems, or devices. For example, a breath actuated inhaler device may function as the system model in order to analyze the operation of the inhaler. Alternately, an in vitro, excised, or mechanical large animal lung may be utilized. A respiratory mask designed for human wear may also be selected. System model use will be discussed later in further detail.

Sensor actuator 56 interacts with system model 48 and control means 52. Sensor actuator 56 comprises means for sensing a variety of conditions, such as pressure, flow rate, volume, actuation of system model 48, and other conditions as desired. Control means 52 receives real time control inputs via input line 60, but may also provide output to display devices. Air flow system 10 provides a simple and inexpensive computerized system that can record and play back air flow patterns. The recording is initiated, in one embodiment, by sensor actuator 56, and the storage of the data occurs in a computer memory storage device in control means 52.

Figure 2:
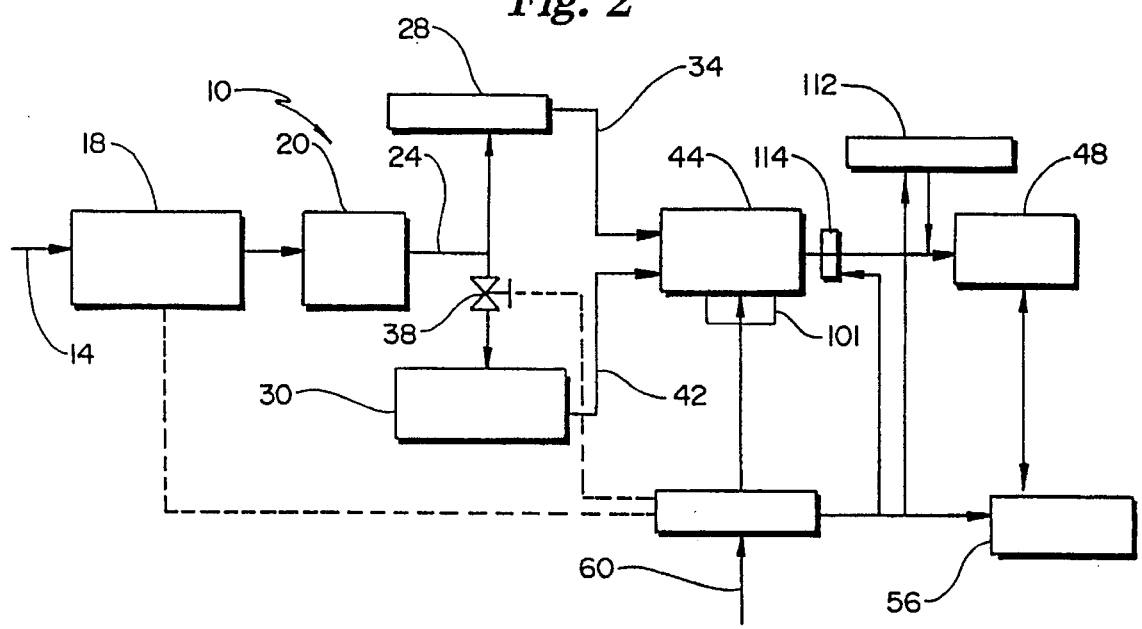
FIG. 2 is a schematic illustration of the air flow system of this invention with optional environmental simulation features.

FIG. 2 is similar to FIG. 1, but it discloses the use of optional environmental simulation components. One embodiment of air flow system 10 comprises connection of a respiratory mask or similar device as system model 48. In this embodiment, air flow system 10 tests the masks under different breathing maneuvers or respiratory conditions. The humidity effect of a particular environment may be quite important for proper mask operation, and is therefore added into system 10, as disclosed in FIG. 2. This permits determination of the resistance and performance of the respiratory system mask under different flow and humidity conditions. FIG. 2 shows humidity component 112 as well as heating component 114 to further simulate the addition of heat to an environmental condition and to replicate or analyze individual or combined effects on air flow patterns.

Figure 3:
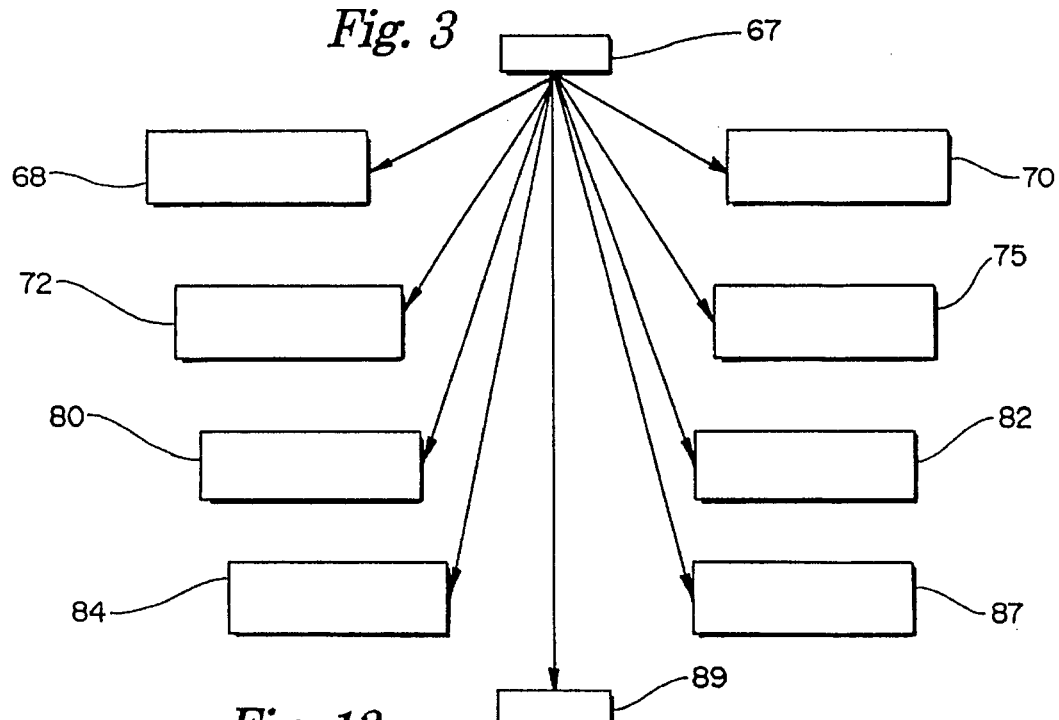
FIG. 3 is a schematic illustration of menu options available on a display screen associated with the air flow system of this invention.
Figure 4:
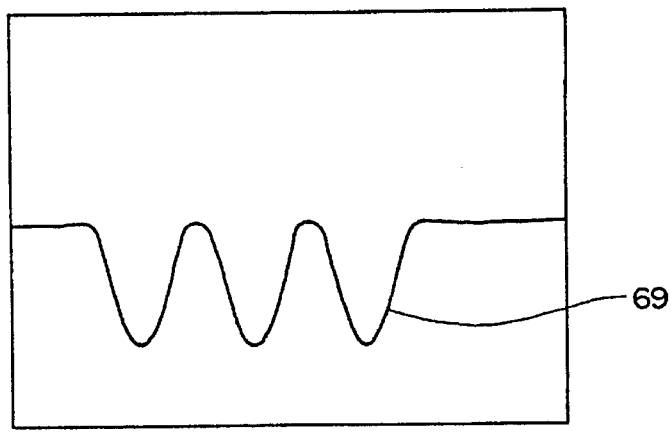
FIG. 4 is a plot of inspiratory breathing cycles.
Figure 5:
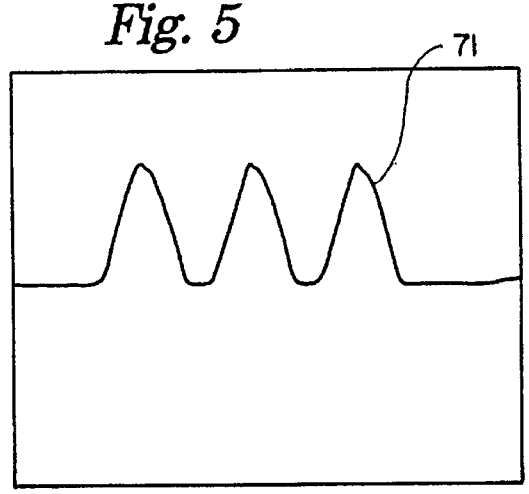
FIG. 5 is a plot of expiratory breathing cycles.

Air flow system 10 is useful to generate various air flow patterns. This is accomplished by selecting one of the options from the software menu as shown in FIG. 3. Module 67 is the entry or start location. Module 68 is the selection module for inspiratory flow. This flow consists of increasing and decreasing negative pressure as shown in plot line 69 of FIG. 4. Module 70 is selected for expiratory flow consisting of increasing and decreasing positive pressure as shown in plot line 71 of FIG. 5. A distinguishing feature of air flow system 10 over any other known systems performing some of the similar functions is the capability to provide distinct and non-mixed positive and negative pressure flow patterns. This is substantially a result of the unique aspiration system, as well as the balancing valve and solenoid valve arrangement.

Figure 7:
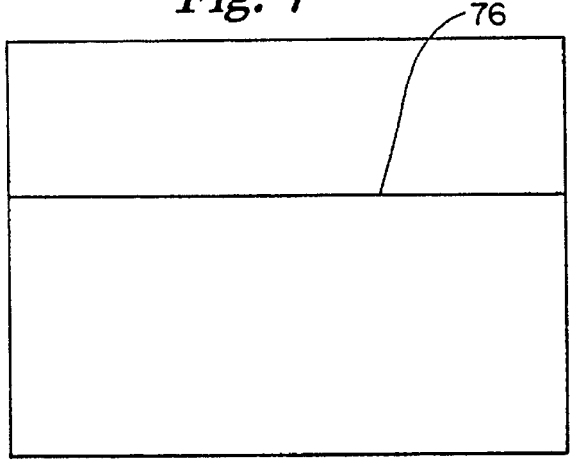
FIG. 7 is a plot of a constant flow breathing pattern.
Figure 6:
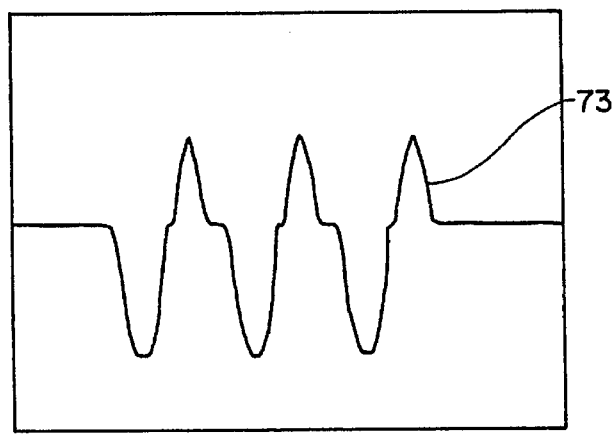
FIG. 6 is a plot of asymmetrical inspiratory and expiratory breathing patterns.

Module 72 is the breath flow module which consists of inspiratory flow, expiratory flow, and a variable breath hold pattern, as shown in asymmetrical fashion in plot line 73 of FIG. 6. Module 75 is a constant flow module which generates a constant flow plot similar to plot line 76 shown in FIG. 7. Module 80 is an increasing ramp flow module of either a negative or positive pressure as shown in plot line 81 of FIGS. 8*a* and 8*b*. Module 82 is similar to module 80 but provides a decreasing ramp flow of either a negative or a positive pressure, as depicted in plot line 83 of FIGS. 9*a* and 9*b*. Module 84 is a variable flow function module which permits input of an entire flow pattern point by point, as shown in plot line 85 of FIG. 10 and plot line 86 of FIG. 11. This option allows very accurate replication and analysis of discrete signal components of a breathing pattern. Plot line 85, for example, is a single frame plot of a recorded flow breathing pattern captured one frame at a time. Plot line 86 is a plot of a selectively reconstructed breathing pattern. Module 87 is a record and playback module for operation for air flow system 10, and FIG. 12 is an example of a plot line 88 generated using this module. All of the modules provide user means for specifying the rate of increase or decrease of the flow rate, the range of flow rate, and the length of breath hold. Menu exit 89 permits exiting of this routine for further operation and control of system 10.

Figure 13:
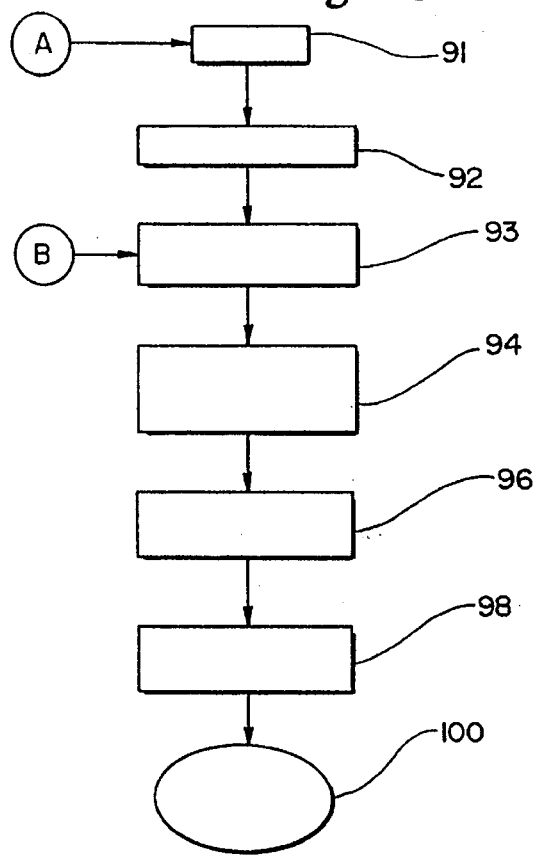
FIG. 13 is a flow diagram of procedures for selectively calibrating the air flow system of the invention for each use.

Software utilized with air flow system 10 and control means 52 preferably accommodates customized data acquisition and analytical capabilities. The air flow generation software in air flow system 10 is preferably divided into at least four menus. A main menu shown in FIG. 3, a calibration menu depicted in FIG. 13, a data generation menu depicted in FIG. 14, and a display analysis menu.

The main menu described above has eight modules that, with the exception of the inspiratory and expiratory modules, which are identical, each comprise calibration and specification menus which are different within each module. The calibration menu starts at module 91 and receives inputs for the desired flow type 92, digital resolution 93, the rate of change of flow rate 94, range of flow rate 96, and number of cycles 98 of flow that need to be generated. A continuation loop 100 permits additional functions. The value for digital resolution depends on the number of bits of the hardware. The flow range is preferably adjusted at balancing valve 38 or via control means 52, or also from the null/gain adjustment ports on a power amp 101 of proportional solenoid valve 44. The digital resolution and flow range determine the sensitivity of the system, and the highest rate of change of flow rate is limited by the mechanical properties of solenoid 44. In this respect, the values for inertia and resistive compliance of solenoid 44 remain far superior to the mechanical time constant limitations or multiple pneumatic source requirements of other systems attempting to record, replicate, or analyze air flow patterns. An example of a mechanical time constant limitation of a bellows system is the limitation due to the incompressibility of gas which limits the performance of such a system. Another example, relating to a cam operated system, is the requirement for such a system to use cam component replacements in order to substantially vary the magnitude of signals between different signal patterns.

Figure 14:
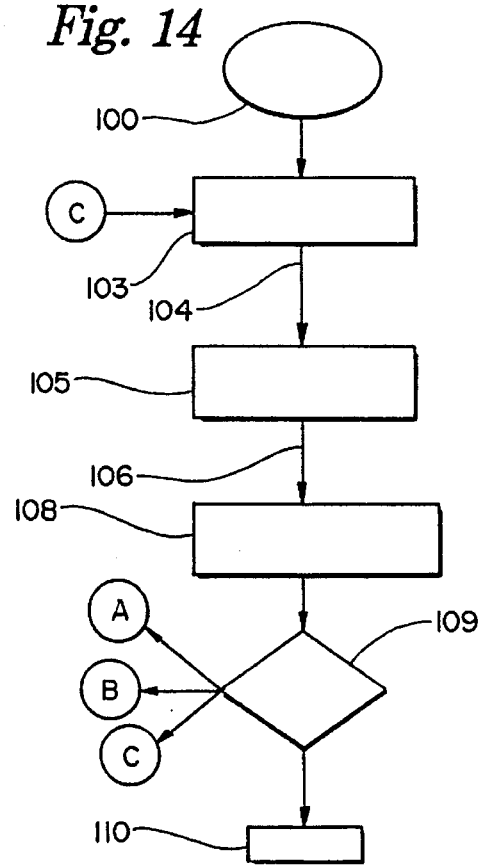
FIG. 14 is a flow diagram of data generation procedures during a data generation mode of operation using the air flow system of this invention.

The data generation menu, FIG. 14, shows operational steps of air flow system 10 in a data generation mode. In this mode, the digital to analog signal output 104 goes from memory or a digital input device 103 to power amp 101 of solenoid 44. Module 105 represents a verification feedback process which generates a digital signal 106 originating with sensor 56. A display of the generated air flow pattern is represented by module 108, which includes access to an analysis menu for analyzing the generated pattern. A repeat function 109 permits repeat loop functioning and access to other menu sites. End option 110 is also shown.

The solenoid valve 44 of the present invention preferably includes a piston member 120, are schematic illustrations of the operation of piston member 120. FIGS. 15–17 designed for selective motion relative to pressure chamber 124, and vacuum chamber 128. Solenoid valve 44, which is depicted in representative form intended to include a variety of actual structures, is designed to provide an efficient rectilinear response pattern relating to pressure and vacuum signals. FIGS. 15 and 17 illustrate piston member 120 in a configuration permitting pressure or vacuum, as shown by flow arrows, depending on the valve lineup, and FIG. 16 illustrates piston member 120 in a neutral position. The configuration of piston member 120 relative to pressure chamber 124, and vacuum chamber 128 allows for very rapid response to various pressure and vacuum signals. This is particularly important for replication of rapidly fluctuating signals, such as a signal produced when a mammal is coughing, hyperventilating, or experiencing other irregular breathing patterns. The frequency response necessary to accurately replicate such air 125 flow patterns is best accomplished using a rapid response valve, such as solenoid valve 44. Other limitations on accurate replication of breathing patterns exist, however the configuration of solenoid valve 44 eliminates many of the recognized and non-recognized limitations present in air flow systems described in various references.

FIG. 18 illustrates a first example of air flow system 10 in which a system model comprises an inhaler 136, such as a breath actuated inhaler useful for controlling airway restrictions and pulmonary functions in humans. The embodiment of FIG. 18 shows air flow system 10 configured for testing or modeling inhaler 136. Inhaler 136 is connectable to sensor actuator 56 for actually testing the performance of inhaler device 136. One example of such testing is to connect inhaler 136 to sensor actuator 56 so that at the time of connection a switch 138 activates control and display subsystem 52 to initiate a vacuum flow through solenoid valve 44 to inhaler 136. This simulates a breath actuation which tests the breath actuation capability of the inhaler device. Air flow system 10 accommodates a range of flow rates and other parameters which are helpful for testing inhaler 136 according to a variety of expected users. The system permits testing for consistency of performance of inhaler 136 at different rates of increase of flow rate. The mechanical properties of inhaler device 136 are also tested using this embodiment through use of a transfer function analysis of output versus input. Then, using a record and playback feature to generate breathing patterns from memory, it is possible to test inhaler device 136 for a simulated or replicated respiratory system disorder.

Air flow system 10 may also be used for in vitro lung models for animals to determine the deposition performance of an aerosol drug in different regions of a lung under a variety of breathing maneuvers or respiratory disorders. A physical model such as a lung cast or a balloon reservoir mechanical model may be used or an actual excised model may be tested. The system may be used to record the breathing patterns of different types of animals, and may even be used to generate abnormal flow patterns from induced airway obstructions to study treatment of the obstructions. Non-linear effects may also be accounted for using air flow system 10 in this manner.

Other embodiments and uses of air flow system 10 include use as: an adaptive respirator, a self-regulated nebulizer, a dynamic calibrator of a spirometer, and a host unit for a portable flow recording unit. In the adaptive respirator configuration, the system may be modified into a real time self-regulated respirator alternating between high pressure and atmospheric pressure or high pressure and low vacuum. The self regulated nebulizer configuration provides an aerosol generator system that generates aerosol by means of an air flow which can be modified to include a valve so that the aerosol is generated only during the inspiratory phase. When the system is used as a dynamic calibrator of a spirometer, it is superior to any similar known system in view of the more precise features and advantages explained earlier in this description. Use of air flow system 10 as a host unit for a portable flow recording unit is described relative to FIG. 19 and FIG. 20.

Figure 19:
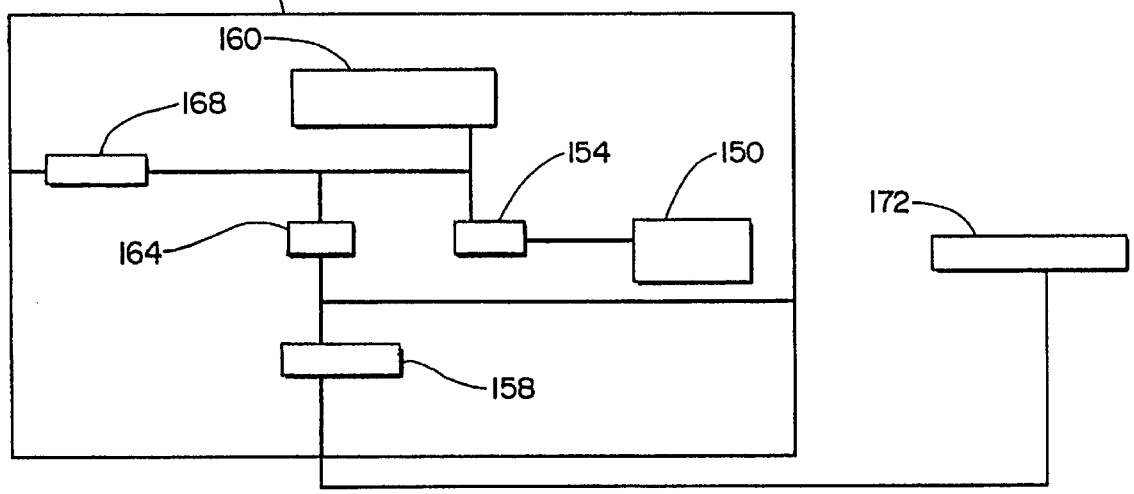
FIG. 19 is a schematic illustration of a portable flow recording unit for use with the air flow system.

FIG. 19 illustrates an optional portable flow recording unit 146 useful for operation with air flow system 10. Portable flow recording unit 146 preferably comprises power means 150 for powering unit 146, memory means 154 for recording and later outputting air flow patterns, sensor means 158 for inputting the airflow patterns, controller means 160 for electronic control, analog to digital converter 164, and electronic interface 168.

Figure 20:
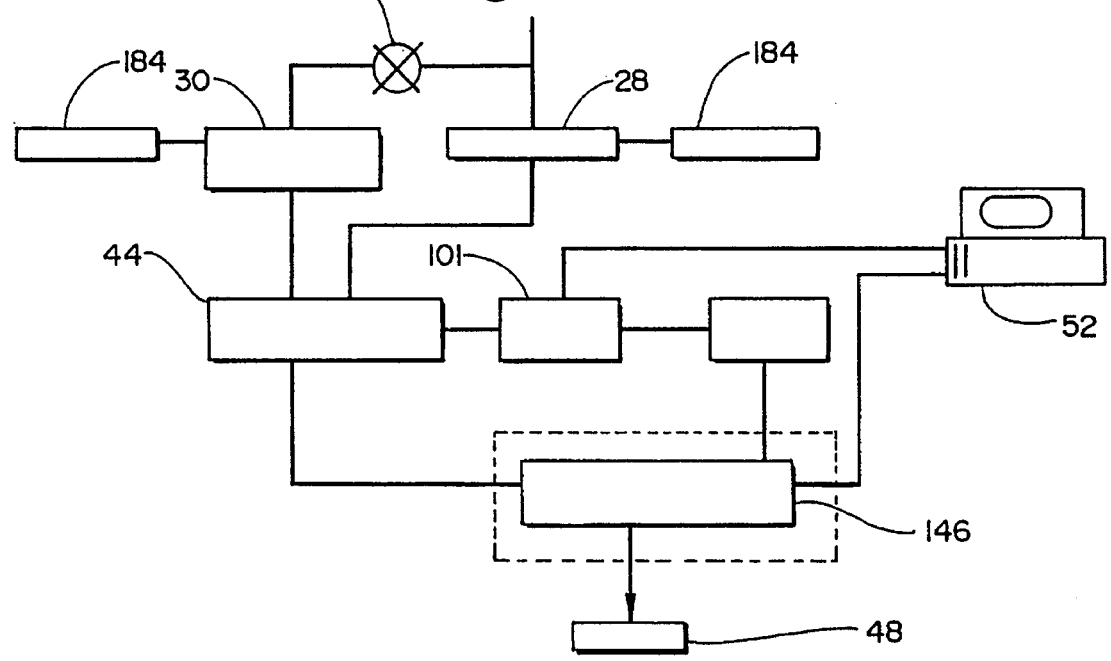
FIG. 20 is an air flow system configured as a flow play-back unit for interaction with the portable flow recording unit of FIG. 19.

Portable flow recording unit 146 is designed for use, preferably, by a human patient in order to input a coughing pattern or other air flow pattern via pneumotach 172 into memory means 154. This permits the human to accurately record the air flow patterns at the onset of a recordable condition, rather than trying to rely on oral description of the symptom at a later time to a medical provider. Using this system, it is possible at a later conference or examination with a medical provider, to record the actual breathing patterns as it naturally occurs and then, to connect portable flow recording unit 146 to air flow system 10, as shown in FIG. 20, and output the recorded air flow pattern. When configured in this manner, the medical provider or other specialist may utilize the analysis and display capabilities of air flow system 10 to determine a proper course of patient treatment for the precise condition recorded at the time of onset. This is a particularly useful embodiment of air flow system 10 in combination with portable flow recording unit 146 in order to timely capture and accurately replicate human conditions which are unpredictable and, for some ailments, frequently occur in the evening or during normal sleep hours. FIG. 20 also discloses use of muffler devices 184 useful for muffling the noise associated with aspirator 28 or reverse aspirator 30.

Additional features and advantages of air flow system 10 combine to permit generation and analysis of complicated air flow patterns. The compact and simple construction of air flow system 10 further enhances its ability to provide relatively inexpensive and simple operation. Additional features and advantages of air flow system 10 include: low frequency recording and playing back of flow maneuvers for mammals; readily available commercial parts; relatively few functional mechanical parts as compared with other air flow systems; ease of portability and connection to remote site sources of air pressure; adjustable rates of change of flow rates; simulation of systems or models exhibiting only inspiratory or expiratory conditions, or systems which exhibit asymmetric and irregular flow patterns; generation of an oscillatory flow which has a base line at a non-zero flow; and no limitation on total lung volume simulation.

What is claimed is:

1. An air flow device for use in recording, analyzing, replicating, and generating, breathing patterns, comprising:
   a) piping structure for receipt and transfer of pressurized gas therethrough, the piping structure having a source connection for receiving a single constant pressure source of pressurized gas;
   b) aspiration means connected to the piping structure for receiving pressurized gas from the source connection and for selectively creating an output pressurization comprising a positive pressure gas flow and a negative pressure gas flow at a proportional solenoid valve;
   c) a balancing valve connected to the piping structure for controlling and calibrating the output pressurization of the aspiration means;
   d) control means for controlling the aspiration means, the balancing valve, and a proportional solenoid valve; and
   e) a proportional solenoid valve mechanically connected to the piping structure with pneumatic input and output connections and electronically connected to the control means with data input and output connections, the proportional solenoid valve providing patterned pneumatic flow between the aspiration means and a system model according to air flow commands received by the proportional solenoid valve from the control means.

2. The device of claim 1, wherein the aspiration means comprises a first aspirator configured for providing a negative pressure output and a second aspirator for providing a positive pressure output.

3. The device of claim 1, further comprising a pressure regulator.

4. The device of claim 1, further comprising an air filter.

5. The device of claim 1, wherein the balancing valve comprises input means for adjusting the peak flow rate of the positive pressure gas flow and the negative pressure gas flow.

6. The device of claim 1, wherein the balancing valve comprises input means for adjusting the symmetry of the gas flow between the positive pressure gas and the negative pressure gas.

7. The device of claim 1, wherein the control means comprises input means for adjusting the symmetry of the gas flow between the positive pressure gas flow and the negative pressure gas flow.

8. The device of claim 1, wherein the proportional solenoid valve receives breathing pattern signals from the control means which operate the proportional solenoid valve to permit flow of the pressurized gas to the system model to replicate a designated breathing pattern.

9. The device of claim 8, wherein the breathing pattern is selected from a list of breathing patterns including an inspiratory, an expiratory, a combined inspiratory and expiratory, a constant flow, an increasing ramp flow, a decreasing ramp flow, and a variable flow pattern.

10. The device of claim 1, further comprising a humidity simulation and detection unit.

11. The device of claim 1, further comprising a temperature simulation and detection unit.

12. An air flow system comprising:
   a) piping structure for receipt and transfer of pressurized gas therethrough, the piping structure having a source connection for receiving a single constant pressure source of pressurized gas;
   b) aspiration means connected to the piping structure for receiving pressurized gas from the source connection and for selectively creating an output pressurization comprising a positive pressure gas flow and a negative pressure gas flow at a proportional solenoid valve;
   c) a balancing valve connected to the piping structure for controlling and calibrating the output pressurization of the aspiration means;
   d) control means for controlling the aspiration means, the balancing valve, and a proportional solenoid valve;
   e) a breath actuated inhaler device; and
   f) a proportional solenoid valve mechanically connected to the piping structure with pneumatic input and output connections and electronically connected to the control means with data input and output connections, the proportional solenoid valve providing patterned pneumatic flow between the aspiration means and the breath actuated inhaler device, the pneumatic flow being controlled and patterned according to air flow commands received by the proportional solenoid valve from the control means.

13. An air flow system according to claim 12, wherein the balancing valve comprises input means for adjusting the peak flow rate of the positive pressure gas flow and the negative pressure gas flow.

* * * * *